(12) United States Patent
Lee et al.

(10) Patent No.: US 6,350,524 B1
(45) Date of Patent: Feb. 26, 2002

(54) HYDROPHILIC POLYURETHANE-COATED CHLORIDE-SELECTIVE ELECTRODES

(75) Inventors: Jin Seo Lee, Seoul; Hyo Jung Yoon, Kyonggi-do, both of (KR); Gang Cui, Keelim-sung (CN); Jae Ho Shin; Hakhyun Nam, both of Seoul (KR); Geun Sig Cha, #4-207 Chungwoon Apt., San 4-25, Chungwoon-dong, Chongno-ku, Seoul 110-030 (KR)

(73) Assignee: Geun Sig Cha, Seoul (KR)

(*) Notice: Subject to any disclaimer, the term of this patent is extended or adjusted under 35 U.S.C. 154(b) by 0 days.

(21) Appl. No.: 09/477,173

(22) Filed: Jan. 4, 2000

(30) Foreign Application Priority Data

Jan. 13, 1999 (KR) .................................................. 99-636

(51) Int. Cl.$^7$ .............................................. B32B 27/40
(52) U.S. Cl. ................................ 428/425.9; 428/424.6; 428/425.5; 209/418; 209/419; 209/435; 205/779; 205/789; 210/500.27
(58) Field of Search ......................... 428/423.1, 425.9, 428/424.6, 425.5; 204/416, 418, 419, 435; 205/778.5, 779, 789; 210/500.27, 500.36, 500.42

(56) References Cited

U.S. PATENT DOCUMENTS

| | | | |
|---|---|---|---|
| 4,199,412 A | 4/1980 | Battaglia et al. | 205/280 |
| 4,534,355 A | * 8/1985 | Potter | 128/365 |
| 5,286,365 A | * 2/1994 | Shu | 204/418 |

OTHER PUBLICATIONS

"Potentionetric behavior of metalloporphyrin–based ion–selective electrodes: Use of silicone rubber matrix for serum chloride analysis", By In Jun Yoon et al., published Feb. 24, 1998.

"Silver/Siver Electrodes Coated with Cellulose Acetate for the Elimination of Bromide and Uric Acid Interferences", no date.

By James R. Sandifer, Analytical Chemistry, vol. 53, No. 8, Jul. 1981.

* cited by examiner

Primary Examiner—Blaine Copenheaver
Assistant Examiner—Christopher Paulraj
(74) Attorney, Agent, or Firm—Bachman & LaPointe, P.C.

(57) ABSTRACT

The present invention relates to chloride-selective electrodes which comprise insoluble metal salt layer and a protecting membrane formed of hydrophilic polyurethane thereon, wherein the hydrophilic polyurethane coated chloride-selective electrodes show fast activation and response time and are usefully employed to accurately measure the chloride by reducing the interference from bromide and iodide or preventing the surface of the electrode from protein adsorption.

6 Claims, 5 Drawing Sheets

HYDROPHILIC POLYURETHANE-COATED CHLORIDE-SELECTIVE ELECTRODES

BACKGROUND OF THE INVENTION

1. Field of the Invention

The present invention relates to chloride-selective electrodes. More particularly, the present invention relates to chloride-selective electrodes comprising insoluble metal salt layer and a protecting membrane formed of hydrophilic polyurethane thereon. The hydrophilic polyurethane coated chloride-selective electrodes show fast activation and response time and are usefully employed to accurately measure the chloride by reducing the interference from bromide and iodide or preventing the surface of the electrode from protein adsorption.

2. Description of the Prior Art

The level of chloride in a liquid is a useful index with which the liquid's state can be perceived and thus, it is very important to fast and accurately measure the chloride levels in physiological fluids such as blood, urine and the like, in domestic water such as tap water and sewage, and in industrial intermediate and final products and by-products, for the purpose of clinical analysis, water examination and product quality analysis, respectively. Particularly, the chloride in serum and whole blood, which compose the majority of extracellular fluid anions, plays an important role in maintaining the osmotic pressure of blood to contribute to the control in blood amount and pressure. Accurate quantitative analysis of the chloride level in blood may yield a vast amount of clinically useful information.

There are reported several quantitative methods for determining chloride levels in blood: mercurimetric titration, argentimetric coulometry, spectrophotometry and potentiometry. The first three methods suffer from serious problems not only of using expensive reagents, but of being subject to a large variation in the analytical results depending on the technicians. What is worse, they are indirect methods requiring isolation of blood cells from blood serum, as makes it difficult to apply them for automated analysis or multi-sample analysis in clinical laboratories.

In contrast, the potentiometry is a direct method that doesn't need such a pretreatment of samples and has apparent advantages over the previous methods in that it is relatively simple in analysis equipment and process, short in analysis time, and inexpensive in analysis cost. Additionally, it is independent of such typical barrier factors as turbidity of solution, hemolysis, bilirubin, etc.

Two types of ion-selective electrodes have been used for the potentiometric determination of blood chloride: solvent polymeric membrane-based electrodes and solid-state membrane-based electrodes.

Typically, a solvent polymeric membrane-based electrode is composed of a polymer such as polyvinyl chloride), polyurethane and silicone rubber, a chloride-selective compound such as metalloporphyrins, quaternary ammonium salts, and organomercuric compounds, and a plasticizer to provide a liquid-like state for the ion-selective material incorporated in the membrane (Anal. Chim. Acta 1998, 367, 175–181). A significant disadvantage of this solvent polymeric membrane-based electrode is that it is quite susceptible to interfering lipophilic anions such as thiocyanate ($SCN_-$) and salicylate, resulting in overestimation.

Another type of a solid-state membrane-based electrode, which uses as an ion-selective electrode membrane an insoluble metal salt layer such as $AgCl$ and $Hg_2Cl_2$, has been typical chloride-selective electrode since the early days of research and it has been reported to be applied in clinical analysis. The solid-state membrane-based electrode can be easily miniaturized because of no internal reference solution and is readily incorporated in any potentiometric analyzers in various formats (e.g., wire, pellet, screen-printed electrodes, tubular electrodes, microchips, etc). In addition, its ability to be readily renewable by simply polishing their deformed or polluted surfaces allows for the provision of stable potentiometric responses for an extended period.

However, its application in clinical analysis has been limited because it suffers not only from a poor discrimination of anions (e.g., bromide and iodide) that form less soluble metal salts than $AgCl$ or $Hg_2Cl_2$, but also from protein adsorption to the electrode surface.

Therefore, in order to effectively use the solid-state membrane-based electrode in clinical analysis, its blood and biocompatibility is required to be improved with reduction in the interference from bromide and iodide. In this regard, it has been suggested that cellulose acetate, poly(acrylic acid), or poly(methacrylic acid) be used as a protective coating on a solid-state membrane electrode (Anal. Chem. 1981, 53, 1164–1170; U.S. Pat. No. 4,199,412, 1980).

It is reported that these protective coatings effectively reduce the interference from bromide and uric acid. Another report gives the data which demonstrate that the biocompatibility of amperometeric sensors is greatly enhanced by modifying their surfaces with cellulose acetate.

The chloride-selective electrode on which a protective coating was made from cellulose acetate is, however, disadvantageous in that it takes a long time to activate and stabilize the electrode, its response time is very slow, ranging from minutes to tens of minutes, and the poor adhesion of cellulose acetate to the electrode surface deteriorates the sensitivity and lifetime of the electrode.

SUMMARY OF THE INVENTION

With this background in mind, the present inventors have intensively and thoroughly conducted research on solid-state membrane-based electrode and found that the use of hydrophilic polyurethane as protective membranes of potentiometric sensors resulted in a fast response time and a great improvement in selectivity for chloride, fast electrode activation, and biocompatibility.

Therefore, it is the object of the present invention to provide chloride-selective electrodes, which provide excellent selectivity for chloride, fast activation and response time, and superior biocompatibility.

In accordance with the present invention, the above and other objects of the present invention could be accomplished by a provision of a solid-state membrane-based chloride-selective electrode, comprising an insoluble metal layer and a protecting membrane formed of hydrophilic polyurethane.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

The present invention pertains to a hydrophilic polyurethane coating on a solid-state membrane-based electrode for the determination of chloride in blood.

The hydrophilicity of the polyurethane coating is controlled by modifying the ratio of poly(ethylene glycol) (hereinafter referred to as "PEG") and polypropylene glycol) (hereinafter referred to as "PPG") when the polyurethane is synthesized. In accordance with the present invention, the molar ratio of PEG and PPG ranges from 1:10 to 10:1 and preferably 1:5 to 5:1.

For use, the polyurethane thus synthesized is dissolved in an organic solvent which is selected from the group consisting of tetrahydrofuran (hereinafter referred to as "THF"), methanol and the mixture thereof.

When it comes to the insoluble metal salt layer, it is made from AgCl, $Hg_2Cl_2$, the mixture thereof, a mixture of AgCl and $Ag_2S$, a mixture of $Hg_2Cl_2$, and $Ag_2S$ or a mixture of AgCl, $Hg_2Cl_2$ and $Ag_2S$. Its fabrication has been achieved by several methods. First, for example, chloridation is done on a silver (Ag) electrode to yield a silver chloride surface. While the ion exchange at the interface between the solution and the ion of insoluble salt thus formed reaches an equilibrium, a potential is produced. Such conversion of silver into silver chloride is typically carried out via two methods: electrochemical method and chemical method. In the former, the silver electrode which is immersed in a sodium chloride or hydrochloric acid solution, is applied with a potential of 0.7 V to convert the silver on the electrode into a silver chloride. The chemical technique comprises chemical oxidation through which the silver surface of the electrode immersed in a $FeCl_3$ or $KCrO_3Cl$ solution is converted into a silver chloride surface.

Another fabrication method of the insoluble metal salt electrodes is to use a mixture of AgCl or $Hg_2Cl_2$ and $Ag_2S$ to produce a pellet electrode under a high pressure. Because the pellet electrode made only of AgCl is mechanically unstable and of low conductivity, $Ag_2S$ is supplemented to reinforce these mechanical and electrochemical weaknesses.

An insoluble metal salt electrode may be fabricated by physically adsorbing an insoluble metal salt onto a metal electrode with the aid of a screen printing method.

A further fabrication method is to apply a metal chloride to a polymeric support to form an insoluble metal salt layer.

A better understanding of the present invention may be obtained in the light of the following examples which are set forth to illustrate, but are not to be construed to limit the present invention.

EXAMPLES I–III

Figure 1:
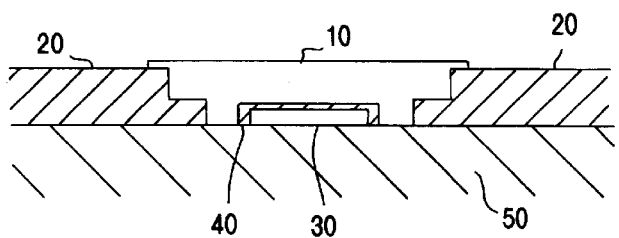
FIG. 1 is a schematic cross section of a solid-state membrane-based chloride-selective electrode coated with a hydrophilic polyurethane membrane.

Fabrication of Chloride-Selective Electrode with Protective Coating of Hydrophilic Polyurethane Silver electrodes were fabricated by screen printing the silver paste on an alumina plate. Then, the silver electrodes were immersed in 0.1 M $FeCl_3$ for 10 min to form AgCl layers. On these layers were overcoated by the THF solution of hydrophilic polyurethane. Thus chloride-selective electrodes for using examples I–III were prepared. With reference to FIG. 1, there is shown a hydrophilic polyurethane membrane-coated silver/silver chloride electrode which is fabricated by a screen printing method. As shown in FIG. 1, first, silver is screen-printed on a predetermined area of an alumina plate 50 covered with an insulating film 20 to form a silver layer 30. Then, this resulting structure is immersed in a $FeCl_3$ solution to create an AgCl layer 40 on the silver layer, followed by coating the AgCl layer 40 with a protective membrane 10.

The compositions of the polyurethane solutions used are given in Table 1, below. Three types of hydrophilic polyurethane were used: Polyurethane A, Polyurethane B and Polyurethane C. The hydrophilicity of these polyurethanes was referred to water uptake (the weight ratios between water absorbed and dry polyurethane: Polyurethane A, 42%; Polyurethane B, 100 %; and Polyurethane C, 206%.

TABLE 1

Composition of Hydrophilic Polyurethane

| Composition | Example I | Example II | Example III |
| --- | --- | --- | --- |
| Polyurethane | HPU[a]-A | HPU[a]-B | HPU[a]-C |
| PEG | 0.005 mol | 0.01 mol | 0.015 mol |
| PPG | 0.015 mol | 0.01 mol | 0.005 mol |
| Desmodur W[b] | 0.052 mol | 0.052 mol | 0.052 mol |
| Ethylene Glycol | 0.03 mol | 0.03 mol | 0.03 mol |
| PEG:PPG | 1:3 | 1:1 | 3:1 |

[a]Hydrophilic polyurethane membrane
[b]Methylene bis(4-cyclohexyl isocyanate)

EXAMPLE IV

Comparison of Stabilization Times for Electrodes

In using ion-selective electrodes in practice, change of their electrochemical responses according to preconditioning time is very important because the response time determines their immediate availability for analysis.

Figure 2:
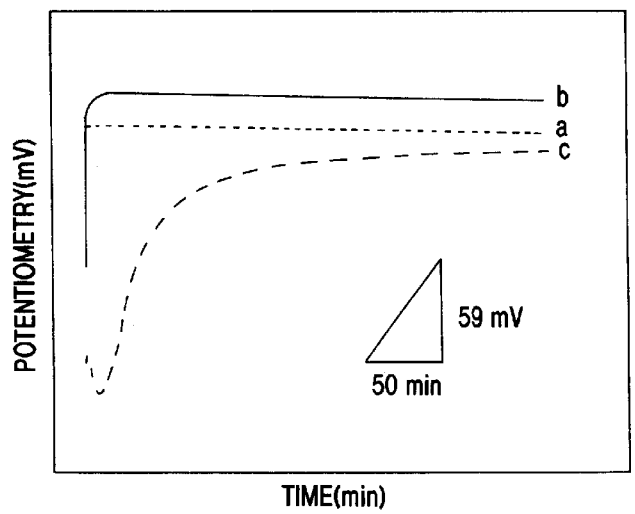
FIG. 2 is a plot showing the changes in potentiometric responses with soaking (preconditioning) time of (a) bare silver/silver chloride electrode, (b) hydrophilic polyurethane membrane-coated electrode and (c) cellulose acetate membrane-coated electrode.

To measure the preconditioning time required for ion-selective electrodes, they were first immersed in a 0.05 M Tris buffer which was titrated to pH 7.4 with $H_2SO_4$ and then, response curves were obtained as shown in FIG. 2. For this three types of ion-selective electrodes were employed: (a) bare silver/silver chloride electrode with no protective membrane; (b) electrode coated with 5% cellulose acetate membrane (which is reported to be most effective); and (c) a hydrophilic polyurethane membrane-coated electrode. The bare chloride-selective electrode had been immersed in the solution exhibited stable potentials immediately. The preconditioning time required for the hydrophilic polyurethane membrane-coated electrode was measured to be less than two minutes, which indicated that the proconditioning time of hydrophilic polyurethane membrane-coated electrode to chloride is almost as fast and stable as the bare silver/silver chloride electrode. For the cellulose acetate-coated electrode, on the other hand, at least 130 minutes was required to reach comparable stable potentials.

Consequently, the long period of time that it takes for the cellulose acetate-coated electrode to show a stable potential makes it difficult to measure chloride immediately on the spot with the electrode because the electrode must be preconditioned for a long time in a sodium chloride-containing solution. Whereas, the hydrophilic polyurethane-modified electrode can be used for the analysis requiring an immediate measurement on the spot by virtue of almost the same fast and stable response to chloride as that of the bare silver/silver chloride electrode.

EXAMPLE V

Response Time and Sensitivity To Chloride

Figure 3:
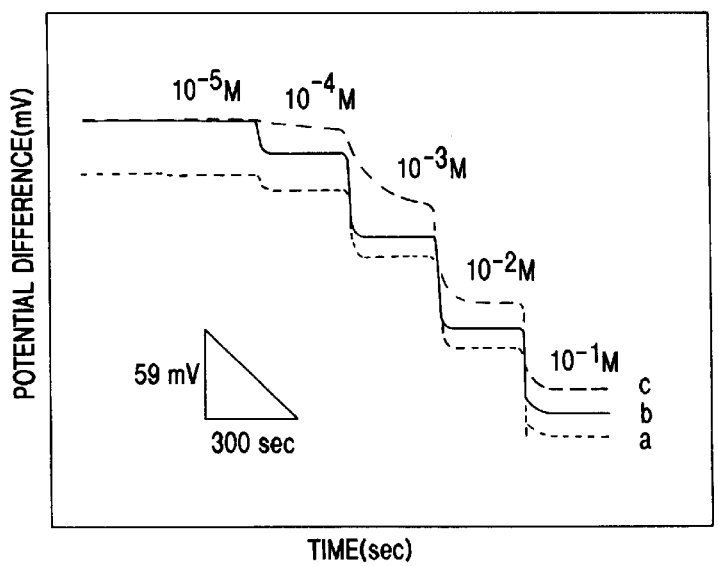
FIG. 3 is a plot showing the potentiometric responses to chloride of (a) bare silver/silver chloride electrode, (b) hydrophilic polyurethane membrane-coated electrode and (c) cellulose acetate membrane-coated electrode.

Potentiometric responses to chloride were measured against time for (a) the bare silver/silver chloride electrode, (b) the hydrophilic polyurethane membrane-coated electrode and (c) the cellulose acetate membrane-coated electrode, and the results are given in FIG. 3. As shown in FIG. 3, the hydrophilic polyurethane membrane-coated electrode potentiometrically responded to chloride at the speed which was indistinguishable from that of the bare silver/ silver chloride electrode while the cellulose acetate membrane-coated electrode was distinctively different in the response time from the above two electrodes. A response slope of 57 mV/decade was measured for the hydrophilic polyurethane membrane-coated electrode, 55 mV/decade for the bare silver/silver chloride electrode and 54 mV/decade for the cellulose acetate membrane-coated electrode. Consequently, the hydrophilic polyurethane membrane-coated electrode is superior in response sensitivity over chloride to the bare silver/silver chloride electrode and the cellulose acetate membrane-coated electrode.

EXAMPLE VI

Response Time and Sensitivity to Bromide

Figure 4A:
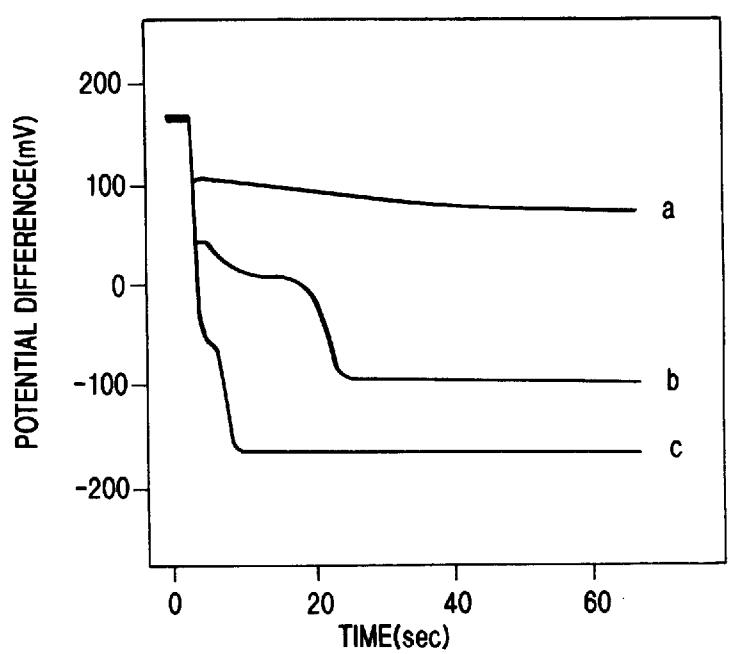
FIG. 4 is a plot showing the potentiometric responses to (a) 1 mM, (b) 10 mM and (c) 100 mM of bromide of (A) bare silver/silver chloride electrode and (B) hydrophilic polyurethane membrane-coated electrode.
Figure 4B:
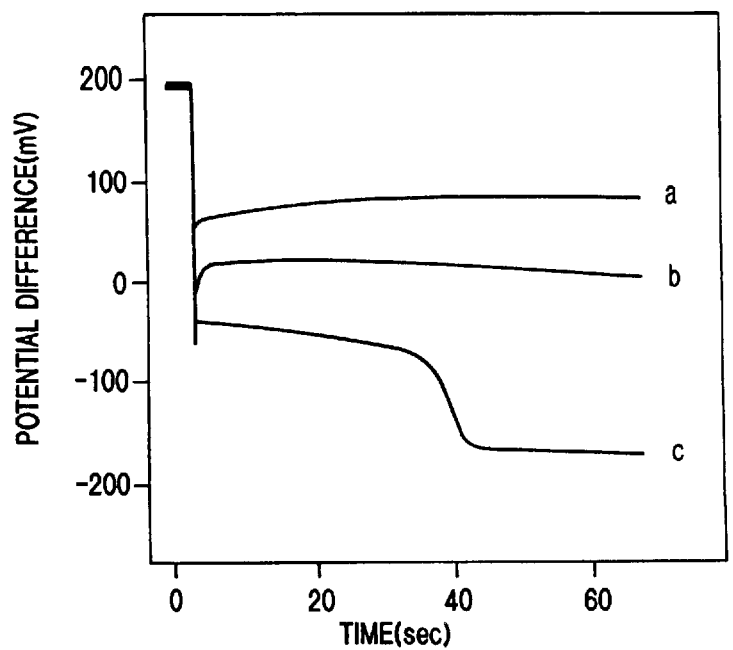

The potentiometric responses of electrodes, which were turned out to be excellent in potentiometric properties to chloride, (A) with and (B) without hydrophilic polyurethane protective membranes to bromide, are shown in FIG. 4. Generally, bromide is Known to be one of the most interfering electrolytes. As apparent from the figure, when being exposed to a 1 mM bromide solution (a), the hydrophilic polyurethane membrane-coated electrode exhibited a stable potential difference while the electrode without the hydrophilic polyurethane membrane was gradually decreased in potential. For a 10 mM bromide solution (b), the hydrophilic polyurethane membrane-coated electrode was still stable in the potentiometric response while the potential of the electrode without the hydrophilic polyurethane membrane was changed slightly (about 38 mV) after 2 min and greatly (about 98 mV) after 10 min. More concentration of bromide, e.g., 100 mM bromide solution (c), made the electrode without the hydrophilic polyurethane membrane to have a great potential change in 2 min, but had no great influence on the potential of the hydrophilic polyurethane membrane-coated electrode until 30 min had /passed. As mentioned previously, this potential change is attributed to the ion exchange at the interface between the solution and the electrode. Therefore, these data demonstrate that hydrophilic polyurethane membrane protects the electrode from the interference from bromide. Likewise, the hydrophilic polyurethane coating keeps other larger anions such as iodide, thiocyanate and salicylate from fouling the electrodes.

EXAMPLE VII

Figure 5:
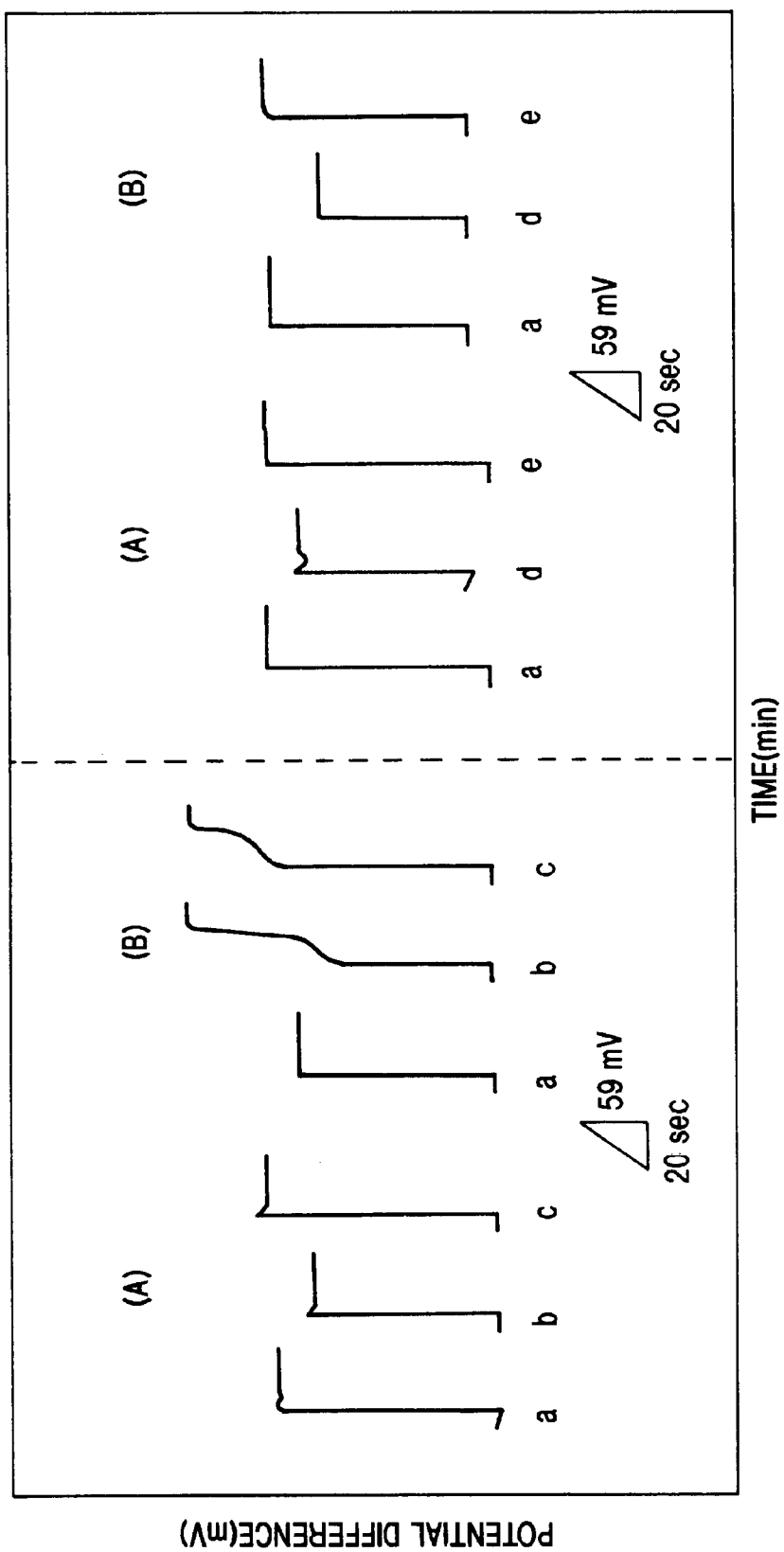
FIG. 5 is a plot showing the potentiometric responses to (a) 100 mM Cl⁻, (b) 10 mM Br⁻, (c) 100 mM Cl⁻+10 mM Br⁻, (d) 3 mM SCN⁻ and (e) 100 mM Cl⁻3 mM SCN⁻ of (A) hydrophilic polyurethane membrane-coated electrode and (B) bare silver/silver chloride electrode.

Response Time and Sensitivity in the Coexistence of Chloride and Interfering Ions In practice, a sample to be analyzed contains both chloride, the target to be quantitated, and other interfering ions. FIG. 5 shows the influence of the interfering ions on the potentiometric responses of the electrodes (A) with and (B) without hydrophilic polyurethane membranes to chloride. In this experiment, 100 mM of chloride, which normal serum contains, was used with overestimated concentrations of interfering ions (bromide 1 mM and 10 mM, thiocyanate 3 mM). For the ease of comparison, 10 mM bromide and 3 mM thiocyanate were used as references in FIG. 5. Instead, the potentials measured for all solutions were calculated into chloride concentrations and listed in Table 2, below.

Regarding the selectivity for chloride over bromide, the hydrophilic polyurethane membrane-coated chloride-selective electrode (A) exerted similar potentiometric responses to all 100 mM chloride solutions irrespective of whether the interfering ions are present or absent. On the other hand, the chloride-selective electrode (B) without the hydrophilic polyurethane membrane resulted in a large error in the presence of the interfering ions. In the case of a solution containing 100 mM chloride and 10 mM bromide, the bare silver/silver chloride electrode (B) showed an overestimated potential which is larger by 95 mV than the accurate value. Even the coexistence of 1 mM bromide induced the bare silver/silver chloride electrode to a large error 147 mM. A solvent polymeric membrane-based chloride-selective electrode employed in commercial analyzers (e.g. Nova Stat Profile Plus 5) reads a similar value (102 mM) of chloride to the accurate value (100 mM) in the presence of 1 mM bromide, but a largely deviated value (124 mM) was read when the commercial electrode was applied for the solution containing 10 mM bromide.

When it comes to the selectivity for chloride over thiocyanate, as shown in FIG. 5, the hydrophilic polyurethane membrane-coated chloride-selective electrode showed a larger potentiometric response in the presence of thiocyanate without chloride than did the electrode without the hydrophilic polyurethane membrane, but was not affected by the thiocyanate which coexisted with chloride. Thus, the response to thiocyanate of the hydrophilic polyurethane membrane-coated electrode itself was not problematic in quantitating the chloride level in clinical samples in practice. In contrast, the bare silver/silver chloride electrode, although low in the response to thiocyanate itself, read an error value (118 mM) of chloride for a practical solution which contained both chloride and thiocyanate. In Table 2, a solvent polymeric membrane-based chloride-selective electrode employed in commercial analyzers (e.g. Nova Stat Profile Ultra M) read a relatively large error (128 mM) of chloride in the presence of 3 mM thiocyanate.

The data obtained in this example demonstrate that the quantitative analysis of chloride by use of the hydrophilic polyurethane membrane-coated chloride-selective electrode is little affected by other interfering anions.

TABLE 2

Quantitation of Chloride with Chloride-Selective Electrodes

| | | Cl Values determined (mM) | | |
|---|---|---|---|---|
| Sample Type | Composition of Sample | Bare Ag/Agcl electrode | HPU[a]-coated electrode | Polymeric membrane electrode[b] |
| Standard Soln | Cl⁻100 mM | 100 | 100 | 99 |
| | Cl⁻100 mM + SCN⁻ 3 mM | 118 | 98 | 128 |
| | Cl⁻100 mM + Br⁻ 1 mM | 147 | 96 | 102 |
| | Cl⁻100 mM + Br⁻ 10 mM | | 100 | 124 |

[a]Hydrophilic polyurethane membrane
[b]The electrode employed in Nova Stat Profile Ultra M (Waltham, MA, USA)

EXAMPLE VIII

Application for Clinical Samples

Figure 6:
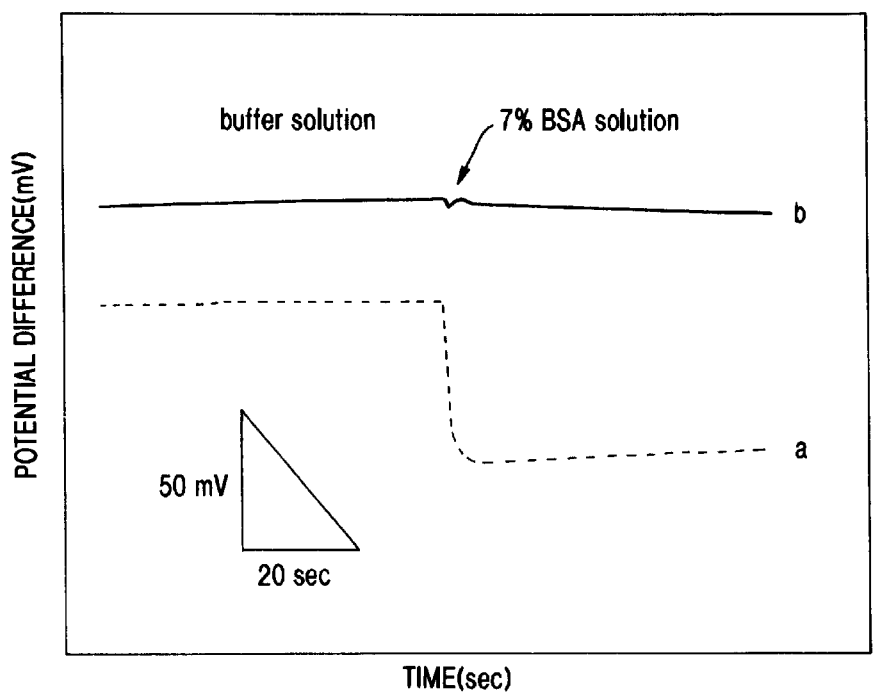
FIG. 6 is a plot showing the effect of protein adsorption on the potentiometric response of (a) bare silver/silver chloride electrode and (b) hydrophilic polyurethane membrane-coated electrode.

A experiment was carried out to know whether the use of the hydrophilic polyurethane membrane reduces the influence of the pollution attributed to the adsorption of macromolecules, such as proteins, to the electrode surface, or not. FIG. 6 shows the result. For this experiment, a 7% bovine serum albumin (BSA) solution was used to determine the potentiometric response of electrodes (a) with and (b) without the hydrophilic polyurethane membranes thereto. As seen in the figure, the bare silver/silver chloride electrode (b) exhibited an abrupt potential change (ca. 68 mV) due to the protein adsorption while the hydrophilic polyurethane membrane-coated electrode exhibited negligible changes before and after the exposure to the sample solution. Therefore, the hydrophilic polyurethane membrane protects the influence of the protein adsorption, giving rise o an increase in the biocompatibility of the electrode.

Figure 7:
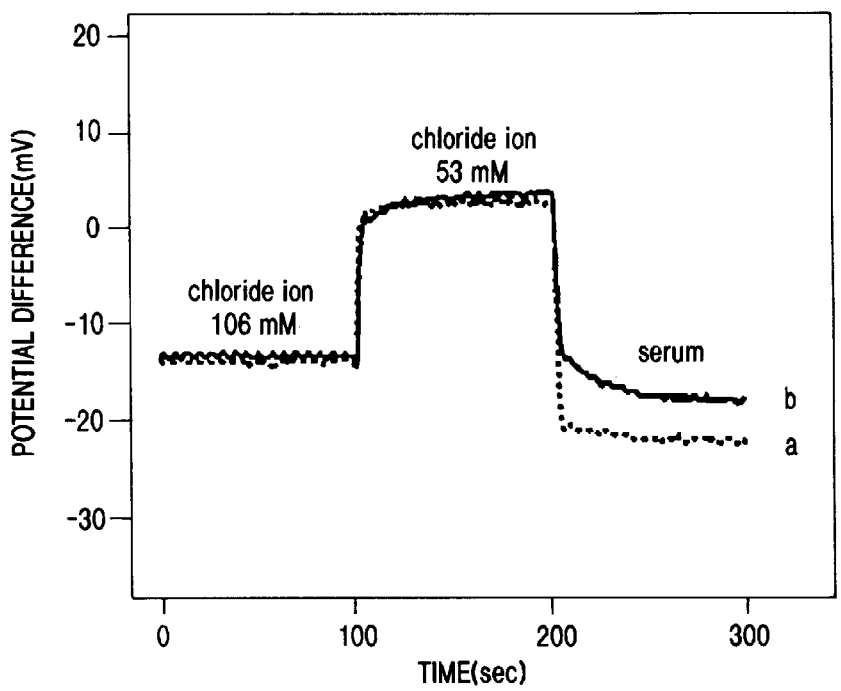
FIG. 7 shows the potentiometric responses to chloride of (a) bare silver/silver chloride electrode and (b) hydrophilic polyurethane membrane-based electrode in a serum sample.
Figure 8:
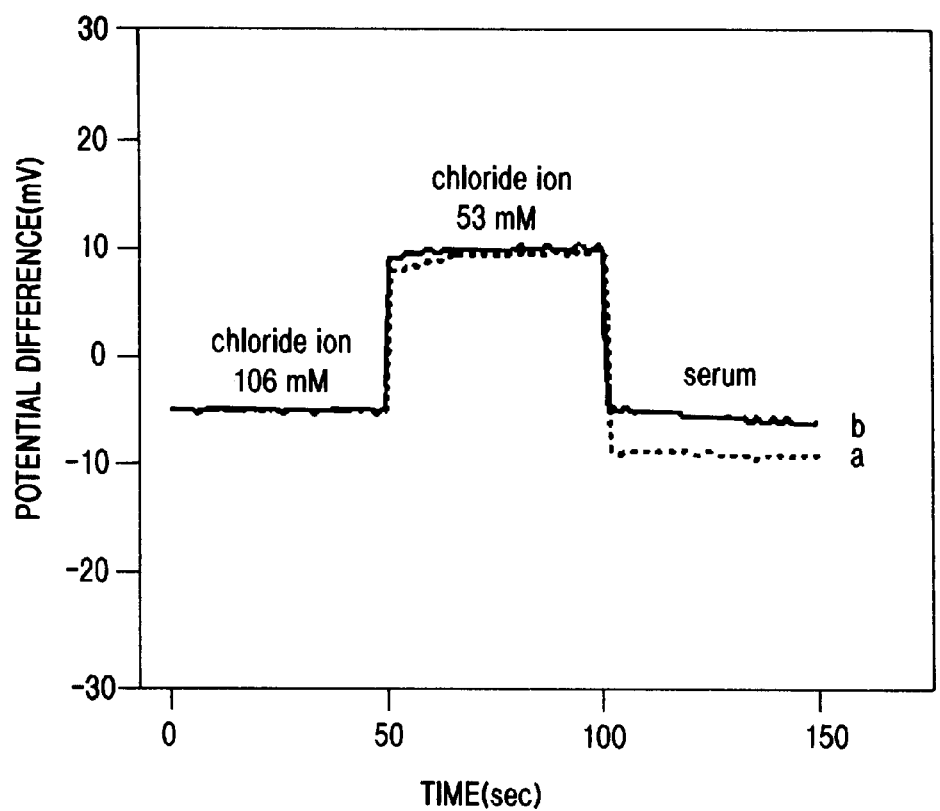
FIG. 8 shows the potentiometric responses to chloride of (a) bare silver/silver chloride electrode and (b) hydrophilic polyurethane membrane-based electrode in a whole blood sample.

In FIGS. 7 and 8, the potentiometric responses of the hydrophilic polyurethane membrane-coated electrode and the bare silver/silver chloride electrode to serum and whole blood are shown. For the conversion of measured potentials into concentrations, two standard calibration solutions (chloride 106 mM and 53 mM) were used, together. Compared to the hydrophilic polyurethane membrane-coated electrode, the bare silver/silver chloride electrode showed larger potentials by about 5 mV for a serum sample and by about 4 mV for a whole blood sample. When being converted into concentrations with reference to the standard calibration solutions, these values corresponded to about 151 mM for the serum sample and to about 125 mM for the whole blood sample. The calculated chloride value for the serum sample, 151 mM, was largely deviated from the specification provided by the manufacturer, 119($\mp$10) mM. For the chloride in the whole blood sample, its value read by the bare silver/silver chloride electrode was larger by 22 mV than that read by a solvent polymeric membrane-based electrode, such as that installed in a commercial analyzer, e.g., Nova Stat Profile Plus clinical analyzer (Waltham). In contrast, the chloride-selective electrode of the present invention provided accurate values, 122 mM for chloride in the serum sample and 105 mM for chloride in the whole blood sample. These quantitated values are given in Table 3, below.

TABLE 3

| | | Cl Values determined (mM) | | |
|---|---|---|---|---|
| Sample Type | Composition of Sample (or Manufacturer's specification) | Bare Ag/AgCl electrode | HPU[a]-coated electrode | Polymeric membrane electrode[b] |
| Serum[c] | Cl⁻119 + 10 mM | 151 | 127 | 122 |
| Whole blood[d] | Cl⁻100 mM + Br⁻ 10 mM | 125 | 105 | 103 |

[a]Hydrophilic polyurethane membrane
[b]The electrode employed in Nova Stat Profile Ultra M (Waltham, MA, USA)
[c]human serum from Nissui Pharmaceutical Co. (Tokyo, Japan)
[d]Obtained from local blood bank Taken together, the data obtained in Examples demonstrate that the chloride-selective electrode coated with the hydrophilic polyurethane membrane according to the present invention is superior in the selectivity for chloride and shows fast electrode activation and immediate response to chloride in addition to accurately measuring chloride in a solution even in the presence of interfering ions such as bromide, iodide, thiocyanate, etc, and macromolecules such as proteins.

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A solid-state membrane chloride-selective electrode, comprising an insoluble metal layer and a protecting membrane, wherein the protecting membrane is formed of hydrophilic polyurethane.

2. A solid-state membrane chloride-selective electrode as set forth in claim 1, wherein the hydrophilic polyurethane comprises poly(ethylene glycol) and poly(propylene glycol) at a molar ratio of 1:10 to 10:1.

3. A solid-state membrane chloride-selective electrode as set forth in claim 1, wherein the hydrophilic polyurethane is dissolved in an organic solvent selected from the group consisting of tetrahydrofuran, methanol and the mixture thereof.

4. A solid-state membrane chloride-selective electrode as set forth in claim 1, wherein the insoluble metal salt layer is selected from the group consisting of AgCl, $Hg_2Cl_2$, a mixture of AgCl and $Hg_2Cl_2$, a mixture of AgCl and $Ag_2S$, a mixture of $Hg_2Cl_2$ and $Ag_2S$, and a mixture of AgCl, $Hg_2Cl_2$ and $Ag_2S$.

5. A solid-state membrane chloride-selective electrode as set forth in claim 1, wherein the insoluble metal salt layer is formed by an electrochemical method; by pressurizing a mixture of (AgCl or $Hg_2Cl_2$) and $Ag_2S$; or by adding a metal chloride in a polymeric support selected from poly(vinyl chloride) and silicone rubber.

6. A solid-state membrane chloride-selective electrode as set forth in claim 1, wherein the electrode is in a form of wire, pellet, a screen-printed electrode, a tubular electrode or a microchip.

* * * * *